United States Patent [19]

Wiedemann et al.

[11] 4,438,128
[45] Mar. 20, 1984

[54] CARDIOACTIVE ARYLOXYPROPANOLAMINES

[75] Inventors: Fritz Wiedemann, Weiheim-Lützelsachsen; Wolfgang Kampe, Heddesheim; Karl Dietmann, Mannheim; Gisbert Sponer, Laudenbach, all of Fed. Rep. of Germany

[73] Assignee: Boehringer Mannheim GmbH, Mannheim, Fed. Rep. of Germany

[21] Appl. No.: 273,543

[22] Filed: Jun. 15, 1981

[30] Foreign Application Priority Data

Jun. 23, 1980 [DE] Fed. Rep. of Germany ....... 3023369

[51] Int. Cl.³ .................. A61K 31/415; C07D 231/54
[52] U.S. Cl. ............................. 424/273 N; 424/251; 424/253; 424/257; 424/263; 424/273 P; 424/330; 544/277; 544/312; 544/317; 548/371; 548/372
[58] Field of Search ................ 548/372, 371; 544/312; 424/273 N

[56] References Cited

U.S. PATENT DOCUMENTS 3,852,291 12/1974 Augstein et al. ................. 544/312
4,143,149 3/1979 Wiedemann et al. .............. 548/372
4,216,314 8/1980 Raabe et al. ...................... 544/312

FOREIGN PATENT DOCUMENTS 281962 11/1978 Fed. Rep. of Germany.

*Primary Examiner*—Paul M. Coughlan, Jr.
*Attorney, Agent, or Firm*—Sprung, Horn, Kramer & Woods

[57] ABSTRACT

The present invention provides aryloxypropanolamines of the general formula:

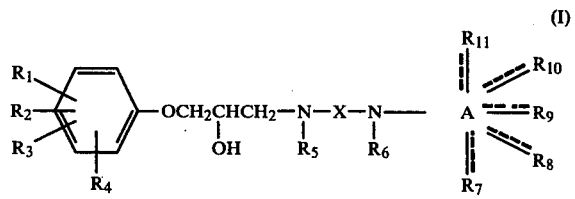

wherein $R_1$, $R_2$, $R_3$ and $R_4$, which may be the same or different, are hydrogen or halogen atoms or lower alkyl, cyano, carboxamido, hydroxyl, lower acyloxy, lower alkoxy, lower alkenyloxy or aryl lower alkoxy radicals, $R_5$ and $R_6$, which may be the same or different, are hydrogen atoms or lower alkyl radicals, X is a straight or branched alkylene chain containing 2 to 6 carbon atoms, A is a mono-, bi- or tricyclic heteroaromatic or hydroheteroaromatic radical or, when at least one of the symbols $R_1$, $R_2$, $R_3$ and $R_4$ is other than a hydrogen atom, may also be a phenyl radical, with the proviso that when A is a uracil-6-yl radical, the 5-position of the uracil moiety does not contain a hydrogen atom, $R_7$, $R_8$, $R_9$, $R_{10}$ and $R_{11}$, which may be the same or different, are mono- or divalent substituents selected from hydrogen, halogen, nitro, hydroxylamino, amino, lower acylamino, lower alkylamino, di-(lower alkyl)-amino, hydroxyethylamino, di-(hydroxyethyl)-amino, hydroxyl, lower alkoxy, allyloxy, methoxy lower alkoxy, cyano, carboxamido, carboxy, lower alkoxycarbonyl, hydroxymethyl, lower alkoxymethyl, halomethyl, aminomethyl, lower acylaminomethyl, di-(lower alkyl)-aminomethyl, pyrrolidinomethyl, piperidinomethyl, di-(hydroxyethyl)-aminomethyl, morpholinomethyl, piperazinomethyl, 4-lower acylpiperazinomethyl, 4-lower alkylpiperazinomethyl, lower alkyl, lower alkenyl, 2-cyanoethyl, 2-(lower alkoxycarbonyl)-ethyl, 2-carboxyethyl, 2-hydroxyethyl, phenyl lower alkyl and phenyl, the phenyl radicals being optionally substituted with 1 or 2 hydroxyl or methoxy radicals, or from oxygen or sulphur; the optically-active forms and the racemic mixtures thereof, and the pharmacologically compatible salts thereof.

The present invention also provides processes for the preparation of these compounds and pharmaceutical compositions containing them.

5 Claims, No Drawings

CARDIOACTIVE ARYLOXYPROPANOLAMINES

The present invention is concerned with aryloxypropanolamines, with processes for the preparation thereof and with pharmaceutical compositions containing them for the prophylaxis and combating of cardiac and circulatory diseases.

In comparison with similar compounds described in Federal Republic of Germany Patent Specifications Nos. 28 19 629 and 28 44 497, a surprising improvement of action can be obtained with the new compounds according to the present invention.

The new compounds according to the present invention have the general formula:

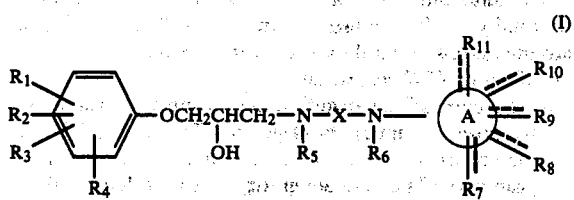

wherein $R_1$, $R_2$, $R_3$ and $R_4$, which may be the same or different, are hydrogen or halogen atoms or lower alkyl, cyano, carboxamido, hydroxyl, lower acyloxy, lower alkoxy, lower alkenyloxy or aryl lower alkoxy radicals, $R_5$ and $R_6$, which may be the same or different, are hydrogen atoms or lower alkyl radicals, X is a straight or branched alkylene chain containing 2 to 6 carbon atoms, A is a mono-, bi- or tricyclic heteroaromatic or hydroheteroaromatic radical or, when at least one of the symbols $R_1$, $R_2$, $R_3$ and $R_4$ is other than a hydrogen atom, may also be a phenyl radical, with the proviso that when A is a uracil-6-yl radical, the substituent in the 5-position of the uracil moiety of the molecule is not a hydrogen atom and $R_7$, $R_8$, $R_9$, $R_{10}$ and $R_{11}$, which may be the same or different, are mono- or divalent substituents selected from hydrogen, halogen, nitro, hydroxylamino, amino, lower acylamino, lower alkylamino, di-(lower alkyl)-amino, hydroxyethylamino, di-(hydroxyethyl)-amino, hydroxyl, lower alkoxy, allyloxy, methoxy lower alkoxy, cyano, carboxamido, carboxy, lower alkoxycarbonyl, hydroxymethyl, lower alkoxymethyl, halomethyl, aminomethyl, lower acylaminomethyl, di-(lower alkyl)-aminomethyl, pyrrolidinomethyl, piperidinomethyl, di-(hydroxyethyl)-aminomethyl, morpholinomethyl, piperazinomethyl, 4-lower acylpiperazinomethyl, 4-lower alkylpiperazinomethyl, lower alkyl, lower alkenyl, 2-cyanoethyl, 2-(lower alkoxycarbonyl)-ethyl, 2-carboxyethyl, 2-hydroxyethyl, phenyl lower alkyl and phenyl, the phenyl radicals being optionally substituted with 1 or 2 hydroxyl or methoxy radicals, or from sulphur or oxygen; and the pharmacologically acceptable salts thereof.

Since the compounds of general formula (I) contain asymmetrical carbon atoms, the present invention also provides the optically-active forms and the racemic mixtures of these compounds.

According to the present invention, the substituent A in the compounds of general formula (I) can be, in particular, the following heteroaromatic radicals: pyrrole, thiophene, oxazole, isoxazole, thiazole, pyrazole, imidazole, 1,2,4-triazole, pyridine, pyrimidine, pyridazine, pyrazine, 1,2,4-triazine, 1,3,5-triazine, thionaphthene, indole, isoindole, benzoxazole, benzthiazole, 1,2-benzisothiazole, benzimidazole, indazole, benztriazole, quinoline, isoquinoline, quinazoline, cinnoline, quinoxaline, phthalazine, carbazole, β-carboline, pyrazolo[3,4-b]pyridine, pyrazolo[2,3-d]-pyrimidine and purine, as well as corresponding hydroheteroaromatic radicals derived therefrom, the attachment to the —X—N($R_6$)— chain being on a cyclic carbon atom or on a cyclic nitrogen atom of the heterocycle.

Hydroheteroaromatic substituents A according to the present invention are partially hydrogenated derivatives of bi- and tricyclic heterocycles, for example, indoline and 1,2,3,4-tetrahydrocarbazole, but not fully hydrogenated monocyclic heterocycles, such as pyrrolidine and piperidine.

The broken line between the symbols $R_7$, $R_8$, $R_9$, $R_{10}$ and $R_{11}$, on the one hand, and ring A in general formulae (I), (III), (V) and (VI), on the other hand, indicates, in each case, a second valency when $R_7$, $R_8$, $R_9$, $R_{10}$ and $R_{11}$ signify a divalent substituent, such as a sulphur or oxygen atom.

The lower alkyl radical in the definitions of the symbols $R_1$–$R_{11}$ and the lower alkyl moiety of lower alkoxy, aryl lower alkoxy, lower alkylamino, di-(lower alkyl)-amino, methoxy lower alkoxy, lower alkoxycarbonyl, lower alkoxymethyl, di-(lower alkyl)-aminomethyl, 4-lower alkylpiperazinomethyl, 2-(lower alkoxycarbonyl)-ethyl and phenyl lower alkyl is to be understood to be a straight-chained or branched radical containing up to 6 and preferably up to 4 carbon atoms, for example, methyl, ethyl, n-propyl, isopropyl, n-butyl, isobutyl, sec.-butyl, tert.-butyl, n-pentyl and n-hexyl radicals, the preferred radicals being the methyl, ethyl, n-propyl, isopropyl and n-butyl radicals.

The lower acyl radical in the lower acyloxy, lower acylamino, lower acylaminomethyl and 4-lower acylpiperazinomethyl radicals is to be understood to be a straight-chained or branched acyl radical containing up to 5 carbon atoms.

The lower alkenyl radical in the substituents $R_7$, $R_8$, $R_9$, $R_{10}$ and $R_{11}$ and in the lower alkenyloxy radicals of the substituents $R_1$, $R_2$, $R_3$ and $R_4$ is to be understood to be a straight-chained or branched, mono- or polyunsaturated chain containing 2 to 5 carbon atoms, the allyl radical being especially preferred.

According to the present invention, the term halogen is to be understood to mean fluorine, chlorine, bromine and iodine-fluorine, chlorine and bromine being preferred.

The aryl moiety of the aryl lower alkoxy radicals in the substituents $R_1$, $R_2$, $R_3$ and $R_4$ is to be understood to be an aromatic ring system containing 6 to 10 carbon atoms, the phenyl radical being especially preferred.

The alkylene chain of the substituent X is to be understood to be a straight or branched chain containing 2 to 6 carbon atoms and preferably 2 to 4 carbon atoms, the ethylene and propylene radicals being especially preferred.

It is obvious that, in cases where the symbol A signifies a grouping which cannot be substituted by more than 3 or 4 of the symbols $R_7$, $R_8$, $R_9$, $R_{10}$ and $R_{11}$, one or two of the substituents $R_7$, $R_8$, $R_9$, $R_{10}$ or $R_{11}$ must be omitted.

The present invention also provides processes for the preparation of the compounds of general formula (I) in which, in known manner, either (a) a compound of the general formula:

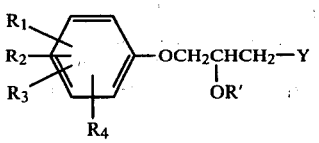

in which $R_1$, $R_2$, $R_3$ and $R_4$ have the same meanings as above, $R'$ is a hydrogen atom or a protective group and $Y$ is a reactive group or $R'$ and $Y$ together represent a valency bond, is reacted with a compound of the general formula:

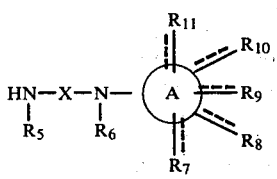

in which $R_5$, $X$, $R_6$, $A$, $R_7$, $R_8$, $R_9$, $R_{10}$ and $R_{11}$ have the same meanings as above; or (b) a compound of the general formula:

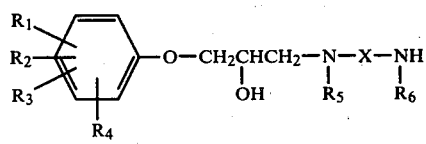

in which $R_1$, $R_2$, $R_3$, $R_4$, $R_5$, $X$ and $R_6$ have the same meanings as above, is reacted with a compound of the general formula:

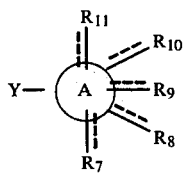

in which $A$, $R_7$, $R_8$, $R_9$, $R_{10}$ and $R_{11}$ have the same meanings as above and $Y$ is a reactive group; or (c) a compound of the general formula:

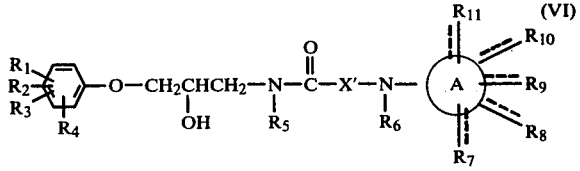

in which $A$, $R_1$, $R_2$, $R_3$, $R_4$, $R_5$, $R_6$, $R_7$, $R_8$, $R_9$, $R_{10}$ and $R_{11}$ have the same meanings as above and $X'$ is a straight or branched alkylene chain containing up to 5 carbon atoms, is reduced and any protective groups which are present are split off by hydrolysis or hydrogenolysis;

and subsequently, if desired, a compound obtained of general formula (I) is converted in known manner into another compound of general formula (I); a racemic mixture of compounds of general formula (I) is, if desired, resolved in known manner into the optically-active forms; and the aryloxypropanolamines obtained of general formula (I) are, if desired, converted by reaction with an inorganic or organic acid into a pharmacologically acceptable salt.

Reactive residues of compounds of general formulae (II) and (V) are, in particular, acid residues of, for example, hydrohalic acids and sulphonic acids, the chlorides, bromides, mesyloxy and tosyloxy residues being especially preferred.

When A represents a heterocycle, further reactive groups Y in compounds of general formula (V) include the methylthio and methylsulphonyl radicals.

The reaction according to variant (a) may be carried out at ambient temperature or with gentle warming, optionally with the use of an inert solvent, it being advantageous to employ the amine component of general formula (III) in excess.

In the case of the reaction according to variant (b), the reaction components of general formulae (IV) and (V) may be reacted in a molar ratio in an inert solvent in the presence of an acid acceptor, for example in boiling toluene in the presence of potassium carbonate.

In variant (c), the reduction of the amide carbonyl group in compounds of general formula (VI) may be carried out with complex hydrides in an inert solvent, for example with lithium aluminum hydride in diethyl ether.

The number of carbon atoms in the radical $X'$ must thereby, in each case, be one less than the number in the radical $X$ of the compound to be prepared of general formula (I).

The protective groups used may be acyl radicals and preferably acetyl or benzoyl radicals, but also tetrahydropyranyl and benzyl protective groups. They may be removed in the manner known from the literature by hydrolysis or hydrogenolysis.

The halohydrins and 2,3-epoxypropoxy derivatives of general formula (II) may be prepared in known manner by reacting appropriate phenols with appropriate reactive $C_3$-components in the presence of a base in an aqueous or aprotic medium, for example by the reaction of a phenol with epichlorohydrin or epibromohydrin in aqueous sodium hydroxide solution or in dimethylformamide or dimethyl sulphoxide in the presence of sodium hydride.

The N-aryl- and N-heteroarylalkylenediamines of general formula (III) may be obtained by aminoalkylation, for example by reacting an aniline or an aminoheterocycle with a phthalimidoalkyl halide in the presence of a base, whereafter the compound (III) is obtained in known manner by hydrazinolysis.

When A in general formula (III) signifies a heterocycle, a reactive compound of general formula (V) may also be reacted with an alkylenediamine, for example, a halo- or methylthiopyrimidine may be reacted with an alkylenediamine which is, as a rule, used in excess.

Compounds of general formula (III) in which A means an indazolyl radical may also be obtained by using the Bucherer-Lepetit reaction, for example, by boiling a 4-hydroxy- or 4-aminoindazole with an excess of an alkylenediamine sulphite in water.

The new compounds of general formula (III), in which A is a mono-, di or tricyclic heteroaromatic or hydroheteroaromatic radical, are valuable intermediates for the preparation of cardiac- and circulatory-active compounds, for example compounds of general formula (I).

Therefore, the present invention also provides the new N-heteroarylalkylenediamines of general formula (III) used herein, as well as the above-described processes for the preparation thereof.

For converting the compounds of general formula (I) into their pharmacologically acceptable salts, these compounds are reacted, preferably in an organic solvent, with an equivalent amount of an inorganic or organic acid, for example, hydrochloric acid, hydrobromic acid, phosphoric acid, sulphuric acid, acetic acid, citric acid, maleic acid, benzoic acid or the like.

The compounds of general formula (I) according to the present invention can be separated into their optically-active forms from their racemic mixtures by known methods via the diastereomeric salts. For resolving the racemates, use can be made, for example, of tartaric acid, malic acid, camphoric acid or camphorsulphonic acid.

The compounds of general formula (I) and their pharmacologically acceptable salts have valuable actions on the heart-circulatory system and, in particular, have cardiotonic and/or β-blocking actions. Therefore, they are useful for the treatment and prophylaxis of cardiac and circulatory diseases.

Therefore, the present invention also provides pharmaceutical compositions containing at least one compound of general formula (I) and/or at least one salt thereof.

For the preparation of pharmaceutical compositions, the compounds of general formula (I) are mixed in known manner with appropriate pharmaceutical carrier materials, aroma, flavoring and coloring materials and formed, for example, into tablets or dragees or, with the addition of appropriate adjuvants, are suspended or dissolved in water or in an oil, for example olive oil.

The new compounds (I) according to the present invention and their salts can be administered enterally or parenterally in liquid or solid form. As injection medium, it is preferred to use water which contains the usual additives for injection solutions, such as stabilizing agents, solubilizing agents or buffers. Additives of this kind include, for example, tartrate and citrate buffers, ethanol, complex formers (such as ethylenediamine-tetraacetic acid and the non-toxic salts thereof) and high molecular weight polymers (such as liquid polyethyleneoxide) for viscosity regulation. Solid carrier materials include, for example, starch, lactose, mannitol, methyl cellulose, talc, highly dispersed silicic acids, high molecular weight fatty acids (such as stearic acid), gelatin, agar-agar, calcium phosphate, magnesium stearate, animal and vegetable fats and solid high molecular weight polymers (such as polyethylene glycols). Compositions suitable for oral administration may, if desired, contain flavoring and/or sweetening agents.

Besides the compounds described in the specific examples, the following compounds are also preferred according to the present invention:

1-phenoxy-3-[2-(1,3-dimethyl-5-isopropylpyrimidine-2,4-dion-6-ylamino)-ethylamino]-propan-2-ol 1-phenoxy-3-[2-(1,3-dimethyl-5-hydroxymethylpyrimidine-2,4-dion-6-ylamino)-ethylamino]-propan-2-ol 1-phenoxy-3-[2-(1,3-dimethyl-5-nitropyrimidine-2,4-dion-6-ylamino)-ethylamino]-propan-2-ol 1-phenoxy-3-[2-(1,3-dimethyl-5-aminopyrimidine-2,4-dion-6-ylamino)-ethylamino]-propan-2-ol 1-phenoxy-3-[2-(1,3-dimethyl-5-methoxypyrimidine-2,4-dion-6-ylamino)-ethylamino]-propan-2-ol 1-phenoxy-3-[2-(1,5-dimethylpyrimidine-2,4(1H,3H)-dion-6-ylamino)-ethylamino]-propan-2-ol 1-phenoxy-3-[2-(1,5-dimethyl-3-ethylpyrimidine-2,4-dion-6-ylamino)-ethylamino]-propan-2-ol 1-phenoxy-3-[2-(1,5-dimethyl-3-allylpyrimidine-2,4-dion-6-ylamino)-ethylamino]-propan-2-ol 1-phenoxy-3-[2-(1,5-dimethyl-3-(3,4-dimethoxybenzyl)-pyrimidine-2,4-dion-6-ylamino)-ethylamino]-propan-2-ol 1-phenoxy-3-[2-(1,5-dimethyl-3-hydroxymethylpyrimidine-2,4-dion-6-ylamino)-ethylamino]-propan-2-ol 1-phenoxy-3-[2-(1,5-dimethyl-3-dimethylaminomethylpyrimidine-2,4-dion-6-ylamino)-ethylamino]-propan-2-ol 1-phenoxy-3-[2-(1,5-dimethyl-3-morpholinomethylpyrimidine-2,4-dion-6-ylamino)-ethylamino]-propan-2-ol 1-phenoxy-3-[2-(1,5-dimethyl-3-carboxamidomethylpyrimidine-2,4-dion-6-ylamino)-ethylamino]-propan-2-ol 1-phenoxy-3-[2-(1,3,5-trimethylpyrimidine-2,4-dion-6-yl-N-methylamino)-ethylamino]-propan-2-ol 1-phenoxy-3-[2-(2,5-dimethylpyrrol-1-ylamino)-ethylamino]-propan-2-ol 1-phenoxy-3-[2-(3,5-dimethylisoxazol-4-ylamino)-ethylamino]-propan-2-ol 1-phenoxy-3-[2-(3,5-dimethylpyrazol-4-ylamino)-ethylamino]-propan-2-ol 1-phenoxy-3-[2-(1,3,4-trimethylimidazol-2-on-5-ylamino)-ethylamino]-propan-2-ol 1-phenoxy-3-[2-(3,5-dimethyl-1,2,4-triazol-4-ylamino)-ethylamino]-propan-2-ol 1-phenoxy-3-[2-(2-aminopyrimidin-4-ylamino)-ethylamino]-propan-2-ol 1-phenoxy-3-[2-(4,6-dimethylpyrimidin-5-ylamino)-ethylamino]-propan-2-ol 1-phenoxy-3-[2-(4,6-dimethyl-2-dimethylaminopyrimidin-5-ylamino)-ethylamino]-propan-2-ol 1-phenoxy-3-[2-(1,2,4,5-tetramethyl-1,2,4-triazin-3-on-6-ylamino)-ethylamino]-propan-2-ol 1-phenoxy-3-[2-(indol-4-ylamino)-ethylamino]-propan-2-ol 1-phenoxy-3-[2-(benzimidazol-4-ylamino)-ethylamino]-propan-2-ol 1-phenoxy-3-[2-(benzimidazol-2-on-4-ylamino)-ethylamino]-propan-2-ol 1-phenoxy-3-[2-(benztriazol-4-ylamino)-ethylamino]-propan-2-ol 1-phenoxy-3-[2-(4-hydroxyisoquinolin-1-ylamino)-ethylamino]-propan-2-ol 1-phenoxy-3-[2-(4-amino-6,7-dimethoxyquinazolin-2-ylamino)-ethylamino]-propan-2-ol 1-phenoxy-3-[2-(4-aminophthalazin-1-ylamino)-ethylamino]-propan-2-ol 1-phenoxy-3-[2-pyrimido[4,5-b]indol-4-ylamino)-ethylamino]-propan-2-ol 1-phenoxy-3-[2-(pyrazolo[3,4-b]pyridin-4-ylamino)-ethylamino]-propan-2-ol 1-phenoxy-3-[2-(5,7-dimethylpyrazolo[3,4-b]pyridin-6(7H)-on-4-ylamino)-ethylamino]-propan-2-ol.

The following examples are given for the purpose of illustrating the present invention. They show some of the numerous possible variants which can be used for the synthesis of the compounds according to the present invention:

EXAMPLE 1

1-Phenoxy-3-[2-(1,2,4-trimethyl-5-pyrazolon-3-ylamino)ethylamino]-propan-2-ol oxalate 3.8 g. Phenyl glycidyl ether are stirred for 22 hours at 70° C. with 8.8 g. 3-(2-aminoethylamino)-1,2,4-trimethyl-5-pyrazolone. The reaction mixture is then dissolved in methylene chloride and purified by column chromatography on silica gel with methylene chloridemethanol (9:1 v/v) and methylene chloride-methanoltriethylamine (20:2:1 v/v/v) as elution agents. There are obtained 5.2 g. (61% of theory) of the free base in the form of an oil.

The free base is dissolved in ethyl acetate and the corresponding oxalate is precipitated out by the addition of an equivalent amount of oxalic acid. This is recrystallized from ethanol, with the use of active charcoal, and is obtained in the form of colorless crystals; m.p. 141°-142° C. (decomp.).

The 3-(2-aminoethylamino)-1,2,4-trimethyl-5-pyrazolone used as starting material can be obtained in the following way:

Diethyl methylmalonate and N,N'-dimethylhydrazine are heated under reflux for 170 hours in methanol in the presence of sodium methylate under an atmosphere of nitrogen. 3-Hydroxy-1,2,4-trimethyl-5-pyrazolone is obtained in the form of colorless crystals which, after recrystallization from ethyl acetate, melt at 87°-89° C.

The above compound is then reacted under reflux with phosphorus oxychloride for 3.5 hours to give the 3,5-dichloro-1,2,4-trimethylpyrazolium salt, which is decomposed with aqueous sodium hydroxide solution, followed by extraction with methylene chloride to give 3-chloro-1,2,4-trimethyl-5-pyrazolone (m.p. 37°-38° C.). This is then heated under reflux for 22 hours with a 15 fold excess of ethylenediamine. After working up the reaction mixture by evaporating, desalting in methanolic solution with the ion exchanger "Amberlite" IRA-400 (OH form) and purifying with silica gel, using methylene chloride-ammoniacal methanol (8:2 v/v) as elution agent, there is obtained, in a yield of 81% of theory, 3-(2-aminoethylamino)-1,2,4-trimethyl-5-pyrazolone in the form of a yellowish oil.

EXAMPLE 2

1-Phenoxy-3-[2-(1,3,5-trimethylpyrazol-4-ylamino)-ethylamino]-propan-2-ol 3.8 g. Phenyl glycidyl ether are left to stand for 48 hours at ambient temperature with 8.4 g. 4-(2-aminoethylamino)-1,3,5-trimethylpyrazole. The reaction mixture is then dissolved in methylene chloride, shaken out with water, dried and purified chromatographically with silica gel, using methylene chloride-ammoniacal methanol (92:8 v/v) as elution agent. After evaporation of the pure fractions, there are obtained 4.7 g. (59% of theory) of the desired free base in the form of an oil.

This oily base is dissolved in ethyl acetate, 1.7 g. fumaric acid is added thereto and the initially greasy precipitate is triturated with isopropyl alcohol and recrystallized from ethanol to give the corresponding fumarate in the form of colorless crystals; m.p. 124° C. (decomp.).

The 4-(2-aminoethylamino)-1,3,5-trimethylpyrazole used as starting material can be obtained as follows: 4-amino-1,3,5-trimethylpyrazole is reacted with N-(2-bromoethyl)-phthalimide in the presence of potassium carbonate in acetonitrile under reflux for 16 hours to give a good yield of 4-(2-phthalimidoethylamino)-1,3,5-pyrazole in the form of yellowish crystals which, after recrystallization from ethanol, melt at 122°-123° C. After subsequent hydrazinolysis, there is obtained 4-(2-aminoethylamino)-1,3,5-trimethylpyrazole in the form of an oil.

EXAMPLE 3

1-Phenoxy-3-[2-(2,4,5-trimethylpyrimidin-6-ylamino)-ethylamino]-propan-2-ol 3.0 g. Phenyl glycidyl ether and 7.2 g. 4-(2-aminoethylamino)-2,5,6-trimethylpyrimidine are stirred for 20 hours at 60° to 70° C. in 5 ml. isopropyl alcohol, whereafter the mixture is separated with a column of silica gel, using methylene chloride-methanol-triethylamine (20:2:1 v/v/v) as elution agent. By recrystallizing from ethyl acetate, with the use of fullers' earth and active charcoal, there are obtained 2.9 g. (44% of theory) of the desired product in the form of colorless crystals; m.p. 119°-121° C.

The 4-(2-aminoethylamino)-2,5,6-trimethylpyrimidine used as starting material (colorless crystals melting at 109°-111° C., after recrystallization from ethyl acetate) can be obtained in good yield by reacting 4-chloro-2,5,6-trimethylpyrimidine with a 15 fold excess of ethylenediamine at ambient temperature for 48 hours.

EXAMPLE 4

1-Phenoxy-3-[2-(3-methyl-2-pyridylamino)-ethylamino]-propan-2-ol

This compound is obtained from phenyl glycidyl ether and 2-(2-aminoethylamino)-3-methylpyridine, in a manner analogous to that described in Example 3, in the form of colorless crystals and in a yield of 33% of theory; m.p. 80°-81° C., after recrystallization from ethyl acetate.

The 2-(2-aminoethylamino)-3-methylpyridine used as starting material is obtained from 2-bromo-3-methylpyridine and a 15 fold excess of ethylenediamine by heating under reflux for 20 hours and is purified by distillation. It is obtained, in a yield of 65% of theory, in the form of a colorless oil; b.p. 81°-83° C./0.01 mm.Hg.

EXAMPLE 5

1-Phenoxy-3-[2-(1,3,5-trimethylpyrimidine-2,4-dion-6-ylamino)-ethylamino]-propan-2-ol 3.4 g. Phenyl glycidyl ether and 9.6 g. 4-(2-aminoethylamino)-1,3,5-trimethylpyrimidine-2,6(1H,3H)-dione are stirred for about 24 hours at 70° C. The reaction mixture is dissolved in methanol and then separated by column chromatography, using a weakly acidic cation exchanger ("Amberlite" CG 50 II pract. (Serva)). The column is pre-treated with about 1.5 liters 0.1 M methanolic triethylammonium acetate solution. The elution agent used is 0.1 M methanolic triethylammonium acetate solution. The fractions containing the pure substance are evaporated, then rendered alkaline with 2 N aqueous sodium hydroxide solution, extracted with methylene chloride and the extracts dried and evaporated. The light colored oil obtained becomes crystalline upon triturating with diethyl ether. After recrystallized from ethyl acetate, there are obtained 3.6 g. (44% of theory) of the desired product in the form of colorless crystals: m.p. 104°-106° C.

The 4-(2-aminoethylamino)-1,3,5-trimethylpyrimidine-2,6(1H.3H)-dione used as starting material can be obtained in the following manner: 22.6 g. 4-chloro-1,3,5-trimethylpyrimidine-2,6(1H,3H)-dione are introduced in small amounts, at 10° to 15° C., into 120 ml. ethylenediamine and the reaction mixture further stirred for 2 hours at ambient temperature. The reaction mixture is then gently evaporated, using a "Rotavapor" at a bath temperature of <35° to 40° C. The product obtained is dissolved in 100 ml. methanol and allowed to run through "Amberlite" IRA-400 (OH form). By gentle evaporation of the solution and then trituration with diethyl ether, there are obtained 18.8 g. (74% of theory) of the desired compound in the form of colorless crystals; m.p. 81°–82° C.

EXAMPLE 6

1-(4-Propoxyphenoxy)-3-[2-(1,3,5-trimethylpyrimidine-2,4-dion-6-ylamino)-ethylamino]-propan-2-ol This compound is obtained in a manner analogous to that described in Example 5 by reacting 4-propoxyphenyl glycidyl ether with 4-(2-aminoethylamino)-1,3,5-trimethylpyrimidine-2,6(1H,3H)-dione. It is obtained in a yield of 32% of theory in the form of colorless crystals which, after recrystallization from methanol, melt at 121°–123° C.

EXAMPLE 7

1-(4-Benzyloxyphenoxy)-3-[2-(2,6-dimethylphenylamino)-ethylamino]-propan-2-ol 5.12 g. 4-Benzyloxyphenyl glycidyl ether and 6.56 g. N-(2,6-dimethylphenyl)-ethylenediamine are heated for 20 hours at 70° C., while stirring. The reaction mixture is worked up by ion exchanger chromatography, using "Amberlite" CG 50 II pract. (Serva) in the manner described in Example 5. There are obtained 6.8 g. (81% of theory) of the desired product in the form of a light colored, viscous oil.

EXAMPLE 8

1-(4-Propoxyphenoxy)-3-[2-(2,6-dimethylphenylamino)-ethylamino]-propan-2-ol 4.15 g. 4-Propoxyphenyl glycidyl ether and 6.6 g. N-(2,6-dimethylphenyl)-ethylenediamine are left to stand for 3 days at ambient temperature and the reaction mixture then separated by ion exchange chromatography in the manner described in Example 5. There are obtained 4.3 g. (58% of theory) of the desired product in the form of colorless crystals; m.p. 51°–54° C. The corresponding neutral fumarate, after recrystallization from ethanol, melts at 168°–169° C.

EXAMPLE 9

1-(3,4-Dimethoxyphenoxy)-3-[2-(1,3,5-trimethylpyrimidine-2,4-dion-6-ylamino)-ethylamino]-propan-2-ol 4.2 g. 3,4-Dimethoxyphenyl glycidyl ether and 8.5 g. 4-(2-aminoethylamino)-1,3,5-trimethylpyrimidine-2,6(1H,3H)-dione in 5 ml. dimethylformamide are left to stand for 48 hours at ambient temperature. The reaction mixture is then dissolved in methylene chloride, shaken out five times with water and the organic phase is extracted with 1 N acetic acid. The aqueous phase is rendered alkaline by the addition of dilute aqueous sodium hydroxide solution and then extracted with methylene chloride. After drying the extract, the solution is chromatographed over silica gel using, as elution agent, methylene chloride-methanol-ammoniacal methanol (saturated) (20.1:1 v/v/v). After evaporating the pure fractions, the residue obtained is recrystallized from ethyl acetate. There are obtained 2.0 g. (24% of theory) of the desired product in the form of colorless crystals; m.p. 103°–104° C.

EXAMPLE 10

The following compounds are obtained in a manner analogous to that described in Example 9:

(a) 1-(4-methoxyphenoxy)-3-[2-(1,3,5-trimethylpyrimidine-2,4-dion-6-ylamino)-ethylamino]-propan-2-ol.

Yield 29% of theory; m.p. 115°–117° C. (after recrystallization from ethyl acetate) from 4-methoxyphenyl glycidyl ether and 4-(2-aminoethylamino)-1,3,5-trimethylpyrimidine-2,6(1H,3H)-dione.

(b) 1-(4-Benzyloxyphenoxy)-3-[2-(1,3,5-trimethylpyrimidine-2,4-dion-6-ylamino)-ethylamino]-propan-2-ol.

Yield 30% of theory; colorless oil from 4-benzyloxyphenyl glycidyl ether and 4-(2-aminoethylamino)-1,3,5-trimethylpyrimidine-2,6(1H,3H)-dione.

(c) 1-(3,4-dibenzyloxyphenoxy)-3-[2-(1,3,5-trimethylpyrimidine-2,4-dion-6-ylamino)-ethylamino]-propan-2-ol.

Yield 32% of theory; colorless oil from 3,4-dibenzyloxyphenyl glycidyl ether and 4-(2-aminoethylamino)-1,3,5-trimethylpyrimidine-2,6(1H,3H)-dione.

EXAMPLE 11

1-Phenoxy-3-[3-(1,3,5-trimethylpyrimidine-2,4-dion-6-ylamino)-propylamino]-propan-2-ol neutral fumarate 3.8 g. Phenyl glycidyl ether are left to stand for 20 hours at ambient temperature with 10 g. 4-(3-aminopropylamino)-1,3,5-trimethylpyrimidine-2,6(1H,3H)-dione, whereafter the reaction mixture is chromatographed on silica gel using, as elution agent, methylene chlorideammoniacal methanol (9:1 v/v). After evaporating the pure fractions, the oil obtained (5.5 g.) is mixed in ethyl acetate with 1.7 g. fumaric acid and the salt obtained is recrystalline from ethanol. There are obtained 2.5 g. (23% of theory) of the desired product in the form of colorless crystals; m.p. 132°–133° C.

The 4-(3-aminopropylamino)-1,3,5-trimethylpyrimidine-2,6(1H,3H)-dione (colorless oil) used as starting material can be obtained in good yield by reacting 4-chloro-1,3,5-trimethylpyrimidine-2,6(1H,3H)-dione with a 15 fold excess of 1,3-diaminopropane at 10° to 15° C., followed by gentle working up of the reaction mixture.

EXAMPLE 12

1-Phenoxy-3-[2-(1,3,6-trimethylpyrimidine-2,4-dion-5-ylamino)-ethylamino]-propan-2-ol 2.43 g. Phenyl glycidyl ether and 5.15 g. 5-(2-aminoethylamino)-1,3,6-trimethylpyrimidine-2,4(1H,3H)-dione are left to stand for 24 hours at ambient temperature, whereupon the reaction mixture is separated with silica gel using, as elution agent, methylene chlorideammoniacal methanol (95:5 v/v). The yellowish oil obtained by evaporation of the pure fractions is triturated with ethyl acetate. After subsequent recrystallization from ethyl acetate, there are obtained 2.55 g. (43% of theory) of the desired product in the form of colorless crystals; m.p. 92°–94° C.

The 5-(2-aminoethylamino)-1,3,6-trimethylpyrimidine-2,4(1H,3H)-dione used as starting material can be obtained by the following reactions:

1.

5-(2-Phthalimidoethylamino)-1,3,6-trimethylpyrimidine-2,4(1H,3H)-dione 24.7 g. 5-Amino-1,3,6-trimethylpyrimidine-2,4(1H,3H)-dione, 44.5 g. N-(2-bromoethyl)-phthalimide and 30.2 g. potassium carbonate are stirred in 450 ml. acetonitrile for 4 days in an autoclave at 110° to 130° C. The inorganic salts are filtered off with suction and the filtrate is evaporated. The residue is purified over silica gel using ethyl acetate as elution agent. There are obtained 13.7 g. (27% of theory) of the desired product in the form of colorless crystals; m.p. 178°–180° C.

2.

5-(2-Aminoethylamino)-1,3,6-trimethylpyrimidine-2,4(1H,3H)-dione 11.7 g. of the above phthalimido compound are boiled with 1.92 ml. hydrazine hydrate in 140 ml. ethanol for 2 hours, whereafter the reaction mixture is acidified and further heated for 1 hour. After cooling, phthalic hydrazide is filtered off with suction, the filtrate is evaporated, the residue is dissolved in methanol and the methanolic solution is desalted with an ion exchanger ("Amberlite" IRA-400 (OH form)). For further purification, the solution is evaporated and the residue chromatographed over a silica gel column using, as elution agent, methylene chloride-ammoniacal methanol (9:1 v/v). There are obtained 5.2 g. (71% of theory) of the desired product in the form of a yellowish oil.

EXAMPLE 13

1-Phenoxy-3-[2-(4-indazolylamino)-ethylamino]-propan-2-ol benzoate 3.0 g. Phenyl glycidyl ether and 7.0 g. 4-(2-aminoethylamino)-indazole are dissolved in 7 ml. dimethylformamide by warming and then left to stand for 20 hours at ambient temperature. The reaction mixture is dissolved in methylene chloride, shaken out 10 times with water and dried with anhydrous sodium sulphate. The solution is treated with fullers' earth, evaporated and the residue is dissolved in ethyl acetate and 3.0 g. benzoic acid added thereto. The salt obtained is recrystallized from isopropyl alcohol, with the addition of active charcoal and fuller's earth. There are obtained 3.9 g. (43% of theory) of the desired product in the form of colorless crystals; m.p. 155°–156° C.

The 4-(2-aminoethylamino)-indazole used as starting material can be obtained from 4-hydroxyindazole and a 10 fold excess of ethylenediamine sulphite in a yield of 43% of theory, the reaction being carried out by heating under reflux for 1 hour in aqueous solution. The desired product is obtained in the form of pale beige crystals which melt at 138°–140° C., after recrystallization from methylene chloride.

EXAMPLE 14

1-(4-Hydroxyphenoxy)-3-[2-(2,6-dimethylphenylamino)-ethylamino]-propan-2-ol neutral fumarate 6.8 g. 1-(4-Benzyloxyphenoxy)-2-[2-(2,6-dimethylphenylamino)-ethylamino]-propan-2-ol are hydrogenated in 100 ml. methanol in the presence of 1 g. palladium-charcoal (10%). The viscous mass obtained after suction filtration and evaporation is stirred at an elevated temperature in 300 ml. ethyl acetate with fumaric acid. The salt obtained is recrystallized from water, with the addition of active charcoal. There are obtained 2.7 g. (43% of theory) of the desired product in the form of almost colorless crystals; m.p. 193°–195° C.

EXAMPLE 15

1-(4-Hydroxyphenoxy)-3-[2-(1,3,5-trimethylpyrimidine-2,4-dion-6-ylamino)-ethylamino]-propan-2-ol neutral fumarate The desired product is obtained in the form of colorless crystals, which melt at 213°–215° C. after recrystallization from water, in a manner analogous to that described in Example 14, by hydrogenating 1-(4-benzyloxyphenoxy)-3-[2-(1,3,5-trimethylpyrimidine-2,4-dion-6-ylamino)-ethylamino]-propan-2-ol.

EXAMPLE 16

1-(4-Methoxyphenoxy)-3-[2-(1,3,5-trimethylpyrimidine-2,4-dion-6-ylamino)-ethylamino]-propan-2-ol 4.8 g. 1-(4-Methoxyphenoxy)-3-(2-aminoethylamino)-propan-2-ol, 3.8 g. 4-chloro-1,3,5-trimethylpyrimidine-2,6(1H,3H)-dione and 4.2 g. potassium carbonate are stirred under reflux in 50 ml. toluene for 4 days. The reaction mixture is then evaporated in a vacuum, the residue is stirred with methylene chloride, the inorganic salts are filtered off with suction, the filtrate is again evaporated and the residue is triturated with a mixture of toluene and ethyl acetate (3:1 v/v). By recrystallization from ethyl acetate, with the use of active charcoal and fullers' earth, there are obtained 2.4 g. (31% of theory) of the desired compound in the form of colorless crystals; m.p. 115°–117° C.

The 1-(4-methoxyphenoxy)-3-(2-aminoethylamino)-propan-2-ol used as starting material is obtained in good yield from 4-methoxyphenyl glycidyl ether and an excess of ethylenediamine by heating under reflux for 1 hour, in the form of a pale oil which solidifies.

EXAMPLE 17

1-(4-Fluorophenoxy)-3-[2-(2,6-dimethylphenylamino)-ethylamino]-propan-2-ol 3.36 g. 4-Fluorophenyl glycidyl ether are left to stand for 2 days at ambient temperature with 6.6 g. N-(2,6-dimethylphenyl)-ethylenediamine. The reaction mixture is separated by chromatography on silica gel with the elution agent ethyl acetate-methanol-triethylamine (100:10:1 v/v/v) to give, after evaporation of the pure fractions, 5.0 g. of the desired product in the form of a viscous oil. After dissolving in diethyl ether and adding 2.5 g. benzoic acid, the corresponding benzoate precipitates out and is recrystallized from isopropyl alcohol. The desired product is obtained in a yield of 5.2 g. (57% of theory) in the form of colorless crystals; m.p. 105°–106° C.

EXAMPLE 18

1-(2,5-Dichlorophenoxy)-3-[2-(2,6-dimethylphenylamino)-ethylamino]-propan-2-ol

This compound is obtained, in a manner analogous to that described in Example 17, from 2,5-dichlorophenyl glycidyl ether and N-(2,6-dimethylphenyl)-ethylenediamine, the base obtained crystallizing. The desired product is obtained in a yield of 4.2 g. (55% of theory) in the form of colorless crystals which, after recrystallization from diethyl ether-ligroin, melt at 66°–68° C.

EXAMPLE 19

1-(4-Hydroxyphenoxy)-3-[3-(2,6-dimethyl-phenylamino)-propylamino]-propan-2-ol neutral oxalate 2.5 g. 1-(4-Benzyloxyphenoxy)-3-[3-(2,6-dimethylphenylamino)-propylamino]-propan-2-ol are hydrogenated in 200 ml. methanol in the presence of 0.25 g. palladium-charcoal (10%). The colorless oil (2.0 g.) obtained after suction filtration and evaporation of the filtrate is dissolved in ethanol. By adding an ethanolic solution of oxalic acid, the corresponding oxalate is precipitated out and recrystallized twice from ethanol. There is obtained 1.0 g. (45% of theory) of the desired product in the form of colorless crystals; m.p. 198°–199° C.

The 1-(4-benzyloxyphenoxy)-3-[3-(2,6-dimethyl-phenylamino)-propylamino]-propan-2-ol used as starting material can be obtained by the following reactions:

1. N-(3-Phthalimidopropyl)-2,6-dimethylaniline.

50 g. N-(3-Bromopropyl)-phthalimide and 50 g. 2,6-dimethylaniline are stirred for 5 hours at 100° C. After adding diethyl ether to the reaction mixture, it is filtered off with suction to give 69 g. of the hydrobromide (m.p. 226°–228° C.). The base is liberated from aqueous solution by adding a concentrated aqueous solution of ammonia. There are obtained 48 g. (83% of theory) of the desired product in the form of colorless crystals; m.p. 97°–98° C.

2. N-(2,6-Dimethylphenyl)-1,3-diaminopropane.

By hydrazinolysis of the phthalimido compound and desalting with an ion exchanger, the desired product is obtained as a colorless oil.

3. 1-(4-Benzyloxyphenoxy)-3-[3-(2,6-dimethyl-phenylamino)-propylamino]-propan-2-ol.

4.23 g. 4-Benzyloxyphenyl glycidyl ether, 5.9 g. N-(2,6-dimethylphenyl)-1,3-diaminopropane and 5 ml. isopropyl alcohol are stirred for 24 hours at ambient temperature. The reaction mixture is worked up by chromatography on silica gel.

EXAMPLE 20

1-(3,4-Dihydroxyphenoxy)-3-[2-(2,6-dimethyl-phenylamino)-ethylamino]-propan-2-ol benzoate 7.9 g. 1-(3,4-dibenzyloxyphenoxy)-3-[2-(2,6-dimethylphenylamino)-ethylamino]-propan-2-ol are hydrogenated in 100 ml. methanol in the presence of 0.5 g. palladium-charcoal (10%). The residue obtained after suction filtration and evaporation of the filtrate is dissolved in ethyl acetate, whereafter, by the addition of a solution of 2.5 g. benzoic acid in ethyl acetate, the benzoate is obtained in crystalline form. This is filtered off with suction and recrystallized from ethyl acetate, with the use of fullers' earth. There are obtained 3.3 g. (47% of theory) of the desired product in the form of almost colorless crystals; m.p. 139°–142° C.

The propan-2-ol derivative used as starting material is obtained in the following manner: a mixture of 6.6 g. N-(2,6-dimethylphenyl)-ethylenediamine and 7.2 g. 3,4-dibenzoyloxyphenyl glycidyl ether is left to stand for 2 days at ambient temperature. The reaction mixture is then separated over a column of silica gel using, as elution agent, ethyl acetate-methanol-triethylamine (100:10:1 v/v/v) to give, after evaporation of the pure fractions, 7.9 g. (75% of theory) of the desired product in the form of a colorless oil.

EXAMPLE 21

1-(4-Fluorophenoxy)-3-[2-(1,3,5-trimethylpyrimidine-1,4-dion-6-ylamino)-ethylamino]-propan-2-ol hydrogen fumarate 3.36 g. 4-Fluorophenyl glycidyl ether and 8.5 g. 4-(2-aminoethylamino)-1,3,5-trimethylpyrimidine-2,6-(1H,3H)-dione are dissolved in 10 ml. dimethylformamide and left to stand for 2 days at ambient temperature. The reaction mixture is then poured into 100 ml. water, extracted with methylene chloride, dried and evaporated. The viscous oil obtained is separated by column chromatography using silica gel and, as elution agent, methylene chloride-ammonia-saturated methanol (20:1 v/v). The product obtained by evaporation of the pure fractions is dissolved in 20 ml. ethyl acetate, whereafter 1.8 g. fumaric acid, dissolved in ethanol, is added thereto. After filtering off with suction, the crystalline product obtained is recrystallized from ethanol, with the addition of 0.9 g. fumaric acid and with the use of active charcoal. There are obtained 5.2 g. (52% of theory) of the desired product in the form of colorless crystals; m.p. 163°–167° C.

EXAMPLE 22

1-(2-Cyanophenoxy)-3-[2-(1,3,5-trimethylpyrimidine-2,4-dion-6-ylamino)-ethylamino]-propan-2-ol hydrogen fumarate Reacting and working up in a manner analogous to that described in Example 21, from 2-cyanophenyl glycidyl ether and 4-(2-aminoethylamino)-1,3,5-trimethylpyrimidine-2,6(1H,3H)-dione, there is obtained the desired product in a yield of 37% of theory in the form of colorless crystals which, after recrystallization from ethanol with the addition of some fumaric acid, melt at 164°–167° C.

EXAMPLE 23

1-(3,4-Dihydroxyphenoxy)-3-[2-(1,3,5-trimethylpyrimidine-2,4-dion-6-ylamino)-ethylamino]-propan-2-ol neutral fumarate 10.4 g. 1-(3-dibenzyloxyphenoxy)-3-[2-(1,3,5-trimethylpyrimidine-2,4-dion-6-ylamino)-ethylamino]-propan-2-ol are hydrogenated in 100 ml. methanol in the presence of 1 g. palladium-charcoal (10%). After suction filtration and evaporation, the residue obtained is dissolved in a little ethanol, whereafter an ethanolic solution of 1 g. of fumaric acid is added thereto. After crystallization has taken place, the crystals are filtered off with suction and recrystallized from aqueous ethanol with the addition of 1 g. hydroquinone and with the use of active charcoal. There are obtained 3.5 g. (43% of theory) of the desired product in the form of almost colorless crystals; m.p. 195°–197° C. (decomp.).

The propan-2-ol compound used as starting material is prepared in the following manner: 8.5 g. 3,4-dibenzyloxyphenyl glycidyl ether and 7.2 g. 4-(2-aminoethylamino)-1,3,5-trimethylpyrimidine-2,6(1H,3H)-dione are dissolved in 8 ml. dimethylformamide and left to stand for 2 days at ambient temperature. The reaction mixture is dissolved in methylene chloride, shaken out with a large amount of water, dried and purified by chromatography on silica gel, using ethyl acetate-methanol-methylamine (100:10:2 v/v/v) as elution agent. There are obtained 10.4 g. (77% of theory) of the desired product in the form of a colorless oil.

EXAMPLE 24

1-Phenoxy-3-[2-(1,3-dimethyl-5-ethylpyrimidine-2,4-dion-6-ylamino)-ethylamino]-propan-2-ol hydrogen fumarate 3.3 g. Phenyl glycidyl ether and 10 g. 4-(2-aminoethylamino)-1,3-dimethyl-5-ethylpyrimidine-2,6(1H,3H)-dione are mixed and left to stand for 24 hours at ambient temperature. The reaction mixture is dissolved in methylene chloride and purified chromatographically with silica gel, using the elution agent methylene chloride-ammonia-saturated methanol (9:1 v/v). By evaporation of the pure fractions, there are obtained 5.5 g. of a yellowish oil. This is dissolved in ethyl acetate, whereafter a solution of 1.7 g. fumaric acid in ethyl acetate is added thereto. After crystallization has taken place, the crystals are filtered off with suction and recrystallized from ethanol. There are obtained 2.8 g. (26% of theory) of the desired product in the form of colorless crystals; m.p. 138°-139° C. (bubble formation).

The compound used as starting material can be obtained in the following manner: 30 g. 4-chloro-1,3-dimethyl-5-ethylpyrimidine-2,6(1H,3H)-dione are introduced in small portions at 10°-15° C., with stirring, into 100 ml. ethylenediamine. The reaction mixture is stirred for a further 2 hours at ambient temperature, excess ethylenediamine is removed under gentle conditions on a "Rotavapor" and the residue is dissolved in methanol, desalted with "Amberlite" IRA-400 (OH form), evaporated and the yellowish oil obtained is purified chromatographically on a silica column using, as elution agents, first, methylene chloride-methanol (9:1 v/v) and, second, methylene chloride and ammonia-saturated methanol (9:1 v/v). The pure fractions are evaporated to give 13.2 g. (39% of theory) of the desired product in the form of a viscous, colorless mass.

EXAMPLE 25

1-Phenoxy-3-[2-(1,3-dimethyl-5-n-butylpyrimidine-2,4-dion-6-ylamino)-ethylamino]-propan-2-ol sesquihydrogen fumarate 5.5 g. 4-Chloro-1,3-dimethyl-5-n-butylpyrimidine-2,6(1H,3H)-dione and 5.0 g. 1-phenoxy-3-(2-aminoethylamino)-propan-2-ol are stirred for 4 days at 80° C. in 20 ml. dimethylformamide. The reaction mixture is then evaporated and the residue is dissolved in methylene chloride, shaken out with water, dried and purified chromatographically with a silica gel column using, as elution agent, methylene chloride-methanol (9:1 v/v). By evaporating the pure fractions, there are obtained 4.4 g. of a yellowish oil. This is dissolved in ethyl acetate and mixed with a solution of 1.3 g. fumaric acid in ethyl acetate. After crystallization has taken place, the crystals are filtered off with suction and subsequently washed with ethyl acetate. There are obtained 2.4 g. (17% of theory) of the desired product in the form of colorless crystals which sinter at 76° C. and melt at 78°-80° C., with the formation of bubbles.

EXAMPLE 26

1-Phenoxy-3-[2-(1,3-dimethyl-5-phenylpyrimidine-2,4-dion-6-ylamino)-ethylamino]-propan-2-ol hydrogen fumarate 5.0 g. 4-Chloro-1,3-dimethyl-5-phenylpyrimidine-2,6(1H,3H)-dione, 4.2 g. 1-phenoxy-3-(2-aminoethylamino)-propan-2-ol and 3.5 ml. N-ethyldiisopropylamine are heated under reflux for 48 hours in 20 ml. acetonitrile. The reaction mixture is then evaporated, the residue is taken up in methylene chloride and the solution is shaken with 2 N aqueous sodium hydroxide solution, dried and separated by column chromatography on silica gel using, as elution agent, methylene chloride-methanol-ammonia-saturated methanol (40:1:1 v/v/v). The oil (5.3 g.) obtained by evaporation of the pure fractions is dissolved in 10 ml. ethyl acetate, whereupon the solution is mixed with a solution of 2 g. fumaric acid in 20 ml. ethanol. After crystallization has taken place, the crystals are filtered off with suction and subsequently washed with ethyl acetate. There are obtained 6.7 g. (62% of theory) of the desired product in the form of colorless crystals; m.p. 181°-183° C.

EXAMPLE 27

1-Phenoxy-3-[2-(1,3-dimethyl-5-cyanopyrimidine-2,4-dion-6-ylamino)-ethylamino]-propan-2-ol hydrochloride 5 g. 4-Chloro-5-cyano-1,3-dimethylpyrimidine-2,6(1H,3H)-dione are added in small portions, with cooling, to a solution of 5.26 g. 1-phenoxy-3-(2-aminoethylamino)-propan-2-ol in 20 ml. dimethylformamide. The reaction mixture is stirred for 2 hours at ambient temperature, mixed with 60 ml. isopropyl alcohol, filtered with suction and the solid obtained subsequently washed with isopropyl alcohol. There are obtained 8.7 g. (85% of theory) of the desired product in the form of colorless crystals; m.p. 202°-204° C.

EXAMPLE 28

1-Phenoxy-3-[2-(1,3-diethyl-5-methylpyrimidine-2,4-dion-6-ylamino)-ethylamino]-propan-2-ol hydrogen fumarate 3.8 g. Phenyl glycidyl ether and 9.8 g. 4-(2-aminoethylamino)-5-methyl-1,3-diethylpyrimidine-2,6(1H,3H)-dione are dissolved in 10 ml. dimethylformamide and left to stand for 24 hours at ambient temperature. The reaction mixture is then poured into water, extracted with methylene chloride, dried and chromatographed on silica gel using, as elution agent, methylene chloridemethanol (9:1 v/v). The yellowish oil (6.8 g.) obtained by evaporation of the pure fractions is dissolved in ethyl acetate, whereafter a solution of 2.1 g. fumaric acid in ethyl acetate is added thereto. The crystalline precipitate obtained is filtered off with suction and washed with ethyl acetate. There are obtained 5.4 g. (42% of theory) of the desired product in the form of colorless crystals which melt at 141°-142° C., with bubble formation.

EXAMPLE 29

1-Phenoxy-3-[2-(1,3,5-trimethylpyrimidine-2,4-dion-6-ylamino)-ethyl-N-methylamino]-propan-2-ol hydrogen fumarate 4.7 g. 4-Chloro-1,3,5-trimethylpyrimidine-2,6-(1H,3H)-dione and 5.6 g. 1-phenoxy-3-(2-aminoethyl)-N-methylamino-propan-2-ol are stirred, in the presence of 3.2 g. N-ethyldiisopropylamine, in 30 ml. toluene for 24 hours at 90° C. The reaction mixture is evaporated and the residue is taken up in ethyl acetate, shaken out with water, dried and chromatographed on silica gel using, as elution agent, ethyl acetate-methanol (10:1 v/v). By evaporation of the pure fractions, there are obtained 4.0 g. of an oil which is dissolved in ethyl acetate. A solution of 1.2 g. fumaric acid in ethyl acetate-ethanol is added thereto and, after crystallization has taken place, the crystals are filtered off with suction and recrystallized from ethanol. There are obtained 2.9 g. (24% of theory) of the desired product in the form of colorless crystals which melt at 166°–167° C.

The compound used as starting material can be obtained by the following reactions:

1. 1-Phenoxy-3-(2-phthalimidoethyl-N-methylamino)-propan-2-ol.

from phenyl glycidyl ether and N-(2-methylaminoethyl)-phthalimide, in the form of a bright yellow oil;

2. 1-Phenoxy-3-(2-aminoethyl-N-methylamino)-propan-2-ol by hydrazinolysis and subsequent desalting with "Amberlite" IRA-400 (OH form), in the form of a bright yellow oil.

EXAMPLE 30

1-Phenoxy-3-[2-(1,3,5-trimethylpyrimidine-2,4-dion-6-yl-N-methylamino)-ethyl-N'-methylamino]-propan-2-ol 4.7 g. 4-Chloro-1,3,5-trimethylpyrimidine-2,6(1H,3H)-dione and 6.0 g. 1-phenoxy-3-(2-methylaminoethyl-N-methylamino)-propan-2-ol (b.p. 138°–142° C./0.01 mm.Hg; obtained from phenyl glycidyl ether and N,N'-dimethylethylenediamine) are stirred for 72 hours at 80° C. in 10 ml. pyridine. The reaction mixture is then dissolved in methylene chloride, washed with water, dried and chromatographed on silica gel using, as elution agent, methylene chloride-methanol (20:1 v/v). By evaporation of the pure fractions, there are obtained 3.0 g. (31% of theory) of the desired product in the form of an almost colorless oil.

EXAMPLE 31

1-Phenoxy-3-[3-(1,3,5-trimethylpyrimidine-2,4-dion-6-ylamino)-2,2-dimethylpropylamino]-propan-2-ol 4.5 g. 4-Chloro-1,3,5-trimethylpyrimidine-2,6(1H,3H)-dione and 6.1 g. 1-phenoxy-3-(3-amino-2,2-dimethylpropylamino)-propan-2-ol (b.p. 159°–161° C./0.01 mm.Hg; obtained from phenyl glycidyl ether and 2,2-dimethyl-1,3-diaminopropane) are stirred for 50 hours at 80° C. in 8 ml. pyridine. The reaction mixture is taken up in methylene chloride, shaken with water, dried, evaporated and the residue obtained chromatographed on silica gel in the manner described in Example 29 to give 2.3 g. (24% of theory) of the desired product in the form of colorless crystals; m.p. 111°–112° C., after recrystallization from ethyl acetate.

EXAMPLE 32

1-Phenoxy-3-[4-(1,3,5-trimethylpyrimidine-2,4-dion-6-ylamino)-butylamino]-propan-2-ol neutral fumarate 4.5 g. Phenyl glycidyl ether and 12.0 g. 4-(4-aminobutylamino)-1,3,5-trimethylpyrimidine-2,6(1H,3H)-dione are mixed and left to stand for 48 hours at ambient temperature. The reaction mixture is then separated chromatographically and salt formation is carried out in the manner described in Example 29. There are obtained 2.6 g. (19% of theory) of the desired product in the form of colorless crystals; m.p. 148°–150° C., with bubble formation.

The 4-(4-aminobutylamino)-1,3,5-trimethylpyrimidine-2,6(1H,3H)-dione used as starting material is obtained in good yield by reacting 4-chloro-1,3,5-trimethylpyrimidine-2,6(1H,3)-dione with an excess of 1,4-diaminobutane (cf. Example 5) in the form of a light yellowish oil.

EXAMPLE 33

1-Phenoxy-3-[2-(1,3,5-trimethylpyrimidin-4-one-2-thion-6-ylamino)-ethylamino]-propan-2-ol hydrogen fumarate 4.3 g. 4-Chloro-1,3,5-trimethylpyrimidin-6(1H)-one-2(3H)-thione are mixed with 4.4 g. 1-phenoxy-3-(2-aminoethylamino)-propan-2-ol and stirred for 24 hours at 60° C. The reaction mixture is purified chromatographically on silica gel using, as elution agent, ethyl acetate methanol (8:2 v/v). By evaporation of the pure fractions, there is obtained an oil (2.9 g.), which is dissolved in ethyl acetate and mixed with a solution of 0.9 g. fumaric acid in ethyl acetate-ethanol. The crystals obtained are filtered off with suction and recrystallized from ethanol. There are obtained 2.0 g. (19% of theory) of the desired product in the form of pale yellow crystals; m.p. 143°–144° C., with bubble formation.

The 4-chloro-1,3,5-trimethylpyrimidin-6(1H)-one-2(3H)-thione used as starting material is obtained in the form of pale yellow crystals (m.p. 128°–129° C., after recrystallization from isopropyl alcohol) in good yield from 4-hydroxy-1,3,5-trimethylpyrimidin-6(1H)-one-2(3H)-thione by reaction with phosphorus oxychloride under reflux for 2 hours.

EXAMPLE 34

1-(4-Propoxyphenoxy)-3-[2-(1,3-dimethylpyrimidin-4-one-2-thion-6-ylamino)-ethylamino]-propan-2-ol 4.8 g. 4-Chloro-1,3-dimethylpyrimidin-6(1H)-one-2-(3H)-thione, 6.7 g. 1-(4-propoxyphenoxy)-3-(2-aminoethylamino)-propan-2-ol and 3.2 g. N-eythyldiisopropylamine are stirred for 24 hours at 90° C. in 30 ml. toluene. The reaction mixture is evaporated and the residue is worked up with a large amount of water. The crystals obtained are filtered off with suction and recrystallized from ethanol, with the use of active charcoal. There are obtained 5.6 g. (53% of theory) of the desired product; m.p. 145°–147° C.

The 1-(4-propoxyphenoxy)-3-(2-aminoethylamino)-propan-2-ol used as starting material is obtained in good yield, as a wax-like mass, from 4-propoxyphenyl glycidyl ether and an excess of ethylenediamine.

EXAMPLE 35

1-Phenoxy-3-[2-(1,3,5-trimethylpyrimidin-2-one-4-thion-6-ylamino)-ethylamino]-propan-2-ol hydrogen fumarate 5.0 g. 1-Phenoxy-3-(2-aminoethylamino)-propan-2-ol and 5.2 g. 4-methylthio-1,3,5-trimethylpyrimidin-2(3H)-one-6(1H)-thione are heated under reflux for 22 hours in 150 ml. isopropyl alcohol. The reaction mixture is then purified chromatographically as described in Example 24. The pale yellowish oil (7.5 g.) obtained is dissolved in ethyl acetate. A solution of 2.3 g. fumaric acid, dissolved in ethyl acetate and ethanol, is added thereto. After crystallization has taken place, the crystals are filtered off with suction and recrystallized from ethanol. There are obtained 5.8 g. (49% of theory) of the desired product in the form of pale yellow crystals which melt at 151°–153° C., with bubble formation.

The 4-methylthio-1,3,5-trimethylpyrimidin-2(3H)-one-6(1H)-thione used as starting material is obtained in good yield by methylating 4-mercapto-1,3,5-trimethylpyrimidin-2(3H)-one-6(1H)-thione, in the form of yellow crystals which melt at 93°-94° C., after recrystallization from ethyl acetate.

EXAMPLE 36

1-Phenoxy-3-[2-(2-methyl-4-hydroxymethylthiophen-3-ylamino)-ethylamino]-propan-2-ol oxalate 0.27 g. Phenyl glycidyl ether, 0.5 g. 3-(2-aminoethylamino)-2-methyl-4-hydroxymethylthiophene and 2 ml. acetonitrile are stirred for 24 hours at 40° C. The reaction mixture is then evaporated and the residue is dissolved in ethanol and mixed with an ethanolic solution of oxalic acid. After crystallization has taken place, the crystals obtained are recrystallized twice from ethanol. There is obtained 0.23 g. (30% of theory) of the desired product, in the form of colorless crystals; m.p. 117°-120° C.

The thiophene derivative used as starting material can be obtained by the following steps:

1. 3-Amino-2-methyl-4-hydroxymethylthiophene; m.p. 70°-71° C. by the reduction of methyl 2-methyl-3-aminothiophene-4-carboxylate with lithium aluminum hydride in diethyl ether.

2. 3-(2-Phthalimidoethylamino)-2-methyl-4-hydroxymethylthiophene; yellowish crystals; m.p. 96°-97° C., after recrystallization from diethyl ether by the reaction of the above compound with N-(2-bromomethyl)-phthalimide in the presence of potassium carbonate for 7 hours at 100° C. in the melt.

3. 3-(2-aminoethylamino)-2-methyl-4-hydroxymethylthiophene; colourless oil by the hydrazinolysis of the 3-(2-phthalimidoethylamino)-thiophene derivative.

EXAMPLE 37

1-Phenoxy-3-[2-(6-chloropyridazin-3-ylamino)-ethylamino]-propan-2-ol

A mixture of 3.0 g. 3,6-dichloropyridazine, 4.2 g. 1-phenoxy-3-(2-aminoethylamino)-propan-2-ol, 3.5 ml. N-ethyldiisopropylamine and 30 ml. toluene is stirred for 24 hours at 100° C. The reaction mixture is then evaporated and the residue is digested simultaneously with 100 ml. water and 100 ml. methylene chloride, followed by suction filtration and recrystallization from isopropyl alcohol, with treatment with fullers' earth. There are obtained 1.4 g. (21% of theory) of the desired product in the form of colorless crystals; m.p. 147°-149° C.

EXAMPLE 38

1-Phenoxy-3-[2-(2-methylquinolin-4-ylamino)-ethylamino]-propan-2-ol

A solution of 4.4 g. phenyl glycidyl ether and 12 g. 2-methyl-4-(2-aminoethylamino)-quinoline in 60 ml. dimethylformamide is left to stand for 48 hours at ambient temperature. The reaction mixture is then taken up in methylene chloride, washed with water, dried and purified chromatographically on a silica gel column using, as elution agent, methylene chloride-methanol-triethylamine (26:3:0.6 v/v/v), and then recrystallized from isopropyl alcohol. There are obtained 3.5 g. (34% of theory) of the desired product in the form of colorless crystals; m.p. 151°-152° C.

The 2-methyl-4-(2-aminoethylamino)-quinoline used as starting material is obtained in good yield by reacting 2-methyl-4-chloroquinoline with an excess of ethylenediamine for 8 hours under reflux. The crude hydrochloride melts at 203°-206° C. Desalting is carried out with the use of an ion exchanger.

EXAMPLE 39

1-Phenoxy-3-[2-(4-methoxyisoquinolin-1-ylamino)-ethylamino]-propan-2-ol 5.2 g. Phenyl glycidyl ether and 15 g. 4-methoxy-1-(2-aminoethylamino)-isoquinoline are dissolved in dimethylformamide and left to stand for 72 hours at ambient temperature. The reaction mixture is then poured into water, extracted with methylene chloride, dried and purified chromatographically on a silica gel column using, as elution agent, methylene chloride-methanol-triethylamine (8:1:0.05 v/v/v). By evaporation of the pure fractions, there are obtained 5.5 g. (44% of theory) of an oil. By the addition of 1.7 g. fumaric acid to a solution of this oil in ethyl acetate-ethanol, a hydrogen fumarate is precipitated out and this is then recrystallized from isopropyl alcohol. The desired product is obtained in the form of colorless cyrstals; m.p. 152°-153° C.

The 4-methoxy-1-(2-aminoethylamino)-isoquinoline used as starting material can be obtained in good yield by reacting 1-chloro-4-methoxyisoquinoline with an excess of ethylenediamine for 12 hours under reflux and desalting with an ion exchanger (OH form).

EXAMPLE 40

1-Phenoxy-3-[2-(2-aminoquinazolin-4-ylamino)ethylamino]-propan-2-ol 3.32 g. Phenyl glycidyl ether and 9.0 g. 2-amino-4-(2-aminoethylamino)-quinazoline are stirred for 24 hours at 50° C. in 100 ml. isopropyl alcohol. The reaction mixture is then evaporated and the residue purified chromatographically in the manner described in Example 38. There are obtained 2.0 g. (26% of theory) of the desired product in the form of a colorless oil.

This oil is taken up in ethyl acetate-ethanol (3:1 v/v) and fumaric acid added thereto, whereupon a fumarate crystallizes out. It is obtained in the form of colorless crystals; m.p. 204°-206° C.

The quinazoline derivative used as starting material can be obtained by the following reactions:

1. 2-Chloro-4-(2-aminoethylamino)-quinazoline is obtained in good yield by reacting 2,4-dichloroquinazoline with an excess of ethylenediamine at 8°-10° C. By reaction thereof with acetic anhydride in methanol, there is obtained 2. 2-chloro-4-(2-acetamidoethylamino)-quinazoline in the form of colorless crystals (m.p. 202°-204° C.), from which, by reaction with liquid ammonia in ethanol (1:2 v/v) in an autoclave for 48 hours at 110° C. and desalting with an ion exchanger (OH form), there is obtained 3. 2-amino-4-(2-acetamidoethylamino)-quinazoline from which, by saponification with 2 N hydrochloric acid for 4 hours under reflux, desalting with ion exchanger (OH form) and chromatographic purification on silica gel, there is obtained 4. 2-amino-4-(2-aminoethylamino)-quinazoline in the form of colorless crystals; m.p. 152°-156° C.

EXAMPLE 41

1-Phenoxy-3-[2-(4-amino-6,7-dimethoxyquinazolin-2-ylamino)-ethylamino]-propan-2-ol 3.8 g. Phenyl glycidyl ether and 10 g. 2-(2-aminoethylamino)-4-amino-6,7-dimethoxyquinazoline are dissolved in 5 ml. dimethylformamide and left to stand for 48 hours at ambient temperature. The reaction mixture is then poured into water, filtered with suction and purified chromatographically on a silica gel column in the manner described in Example 24. There are obtained 2.5 g. (24% of theory) of the desired product in the form of colorless crystals; m.p. 122°–124° C., after recrystallization from isopropyl alcohol.

The 2-(2-aminoethylamino)-4-amino-6,7-dimethoxyquinazoline used as starting material (benzoate: m.p. 207°–208° C., after recrystallization from isopropyl alcohol) is obtained in good yield by reacting 2-chloro-4-amino-6,7-dimethoxyquinazoline with an excess of ethylenediamine for 10 hours at 100° C., desalting with an ion exchanger (OH form) and chromatographic purification in the manner described in Example 24.

EXAMPLE 42

1-Phenoxy-3-[2-(3-methylquinoxalin-2-ylamino)-ethylamino]-propan-2-ol 5.6 g. Phenyl glycidyl ether and 15 g. 2-(2-aminoethylamino)-3-methylquinoxaline are dissolved in a little dimethylformamide and warmed to 40° C. for 32 hours. The reaction mixture is then poured into water, extracted with methylene chloride, dried and purified chromatographically on silica gel in the manner described in Example 25. There are obtained 4.2 g. (33% of theory) of the desired product in the form of a viscous oil.

Fumaric acid is added to a solution of this oil in ethyl acetate. A salt precipitates out which is then recrystallized from ethanol to give colourless crystals of a neutral fumarate hydrate; m.p. 152°–153° C.

The 2-(2-aminoethylamino)-3-methylquinoxaline used as starting material is obtained by reacting 2-chloro-3-methylquinoxaline with a 15-fold excess of ethylenediamine and desalted with an ion exchanger (OH form). The product is obtained in the form of colorless crystals which, after recrystallization from xylene, melt at 60°–61° C.

EXAMPLE 43

1-(4-Fluorophenoxy)-3-[2-(indazol-4-ylamino)-ethylamino]-propan-2-ol benzoate 3.36 g. 4-Fluorophenyl glycidyl ether and 7.0 g. 4-(2-aminoethylamino)-indazole are dissolved in 10 ml. dimethylformamide and left to stand for 2 days at ambient temperature. The reaction mixture is then poured into water, extracted with methylene chloride, dried and purified chromatographically on silica gel in the manner described in Example 24. The residue of the pure fractions is taken up in ethyl acetate, then mixed with 2 g. benzoic acid, filtered off with suction and recrystallized from isopropyl alcohol, with the use of active charcoal. There are obtained 5.6 g. (60% of theory) of the desired product in the form of colorless crystals; m.p. 157°–159° C.

EXAMPLE 44

1-(4-Hydroxyphenoxy)-3-[2-(indazol-4-ylamino)-ethylamino]-propan-2-ol 5.0 g. 1-(4-Benzyloxyphenoxy) 3-[2-(indazol-4-ylamino)-ethylamino]-propan-2-ol are hydrogenated in the presence of 0.5 g. palladium-charcoal (10%) in 100 ml. methanol. After filtering off the catalyst with suction, the filtrate is evaporated and the residue is triturated with ethanol. It is then dissolved in hot dimethylformamide, treated with active charcoal, mixed with double the amount of water, filtered off with suction and washed with water and then with ethanol. There are obtained 3.0 g. (76% of theory) of the desired product in the form of pale, pinkish crystals; m.p. 216°–218° C.

The 1-(4-benzyloxyphenoxy)-3-[2-(indazol-4-ylamino)-ethylamino]-propan-2-ol used as starting material can be obtained in the following manner: 5.1 g. 4-benzyloxyphenyl glycidyl ether and 7.0 g. 4-(2-aminoethylamino)-indazole are dissolved in 10 ml. dimethylformamide and left to stand for 2 days at ambient temperature. The reaction mixture is then digested by the addition of 20 ml. methanol, filtered off with suction and then washed with methanol. There are obtained 5.0 g. (58% of theory) of the desired product in the form of colorless crystals; m.p. 151°–153° C.

EXAMPLE 45

1-Phenoxy-3-[3-(indazol-4-ylamino)-propylamino]-propan-2-ol benzoate 3.0 g. Phenyl glycidyl ether and 7.5 g. 4-(3-aminopropylamino)-indazole are dissolved in 10 ml. dimethylformamide at 60° C. and then left to stand for a day at ambient temperature. The reaction mixture is poured into water, extracted with methylene chloride, dried and purified chromatographically on silica gel in the manner described in Example 21. The viscous residue of the pure fractions (5.3 g.; 78% of theory) is dissolved in a little ethyl acetate, whereafter 2 g. benzoic acid are added thereto, followed by suction filtration and recrystallization from ethanol, with the use of active charcoal. There are obtained 2.8 g. (30% of theory) of the desired product in the form of colorless crystals; m.p. 162°–164° C.

The 4-(3-aminopropylamino)-indazole used as starting material can be obtained in the following manner: sulphur dioxide is passed into a solution of 74 g. 1,3-diaminopropane in 150 ml. water until the pH is 7, whereafter 13.4 g. 4-hydroxyindazole are added thereto and the reaction mixture is heated to 100° C. for 3 hours. By the addition of double the amount of methanol, salts are precipitated out which are filtered off with suction. The filtrate is evaporated and the oily residue is rendered alkaline with a concentrated aqueous solution of ammonia and subsequently extracted with methylene chloride. By evaporation of the extract, there are obtained 7.8 g. (41% of theory) of the desired product in the form of gray crystals; m.p. 154°–163° C.

EXAMPLE 46

1-Phenoxy-3-[2-(indazol-5-ylamino)-ethylamino]-propan-2-ol 3.0 g. Phenyl glycidyl ether and 7.0 g. 5-(2-aminoethylamino)-indazole are dissolved in 10 ml. dimethylformamide by briefly heating to 70° C. and then left to stand for 24 hours at ambient temperature. The reaction mixture is shaken with 400 ml. methylene chloride-methanol (8:2 v/v) and 200 ml. water. The organic phase is evaporated and the residue obtained is purified by column chromatography on silica gel using, as elution agent, methylene chloride-methanol (9:1 v/v) and methylene chloride-ammonia-saturated methanol (9:1 v/v). The residue of the pure fractions is boiled under reflux for 1 hour with 50 ml. ethyl acetate and, after cooling, filtered off with suction and recrystallized from isopropyl alcohol, with the use of active charcoal.

There are obtained 1.7 g. (26% of theory) of the desired product in the form of almost colorless crystals, which sinter at 137° C. and melt at 141°–144° C.

The 5-(2-aminoethylamino)-indazole used as starting material can be obtained in the following manner: a mixture of 12.0 g. 5-aminoindazole, 146 g. ethylenediamine sulphite, 146 ml. water and 10 ml. n-propanol is heated to 100° C. for 24 hours, while stirring. After cooling, the reaction mixture is diluted with 500 ml. methanol. The precipitated salts are filtered off with suction, the filtrate is evaporated and the residue is rendered alkaline by the addition of a concentrated aqueous solution of ammonia. The precipitate is filtered off with suction and washed with water to give 9.4 g. of the desired crystalline product; m.p. 150°–165° C.

EXAMPLE 47

1-Phenoxy-3-[2-(indazol-7-ylamino)-ethylamino]-propan-2-ol 3.0 g. Phenyl glycidyl ether and 7.0 g. 7-(2-aminoethylamino)-indazole are stirred for 10 hours at 70° C. in 20 ml. isopropyl alcohol. The reaction mixture is then evaporated and purified chromatographically on a silica gel column in the manner described in Example 24. The residue of the pure fractions is digested with ethyl acetate and then recrystallized from ethyl acetate, with the use of active charcoal and fullers' earth. There are obtained 2.3 g. (35% of theory) of the desired product in the form of colorless crystals; m.p. 117°–119° C.

The 7-(2-aminoethylamino)-indazole used as starting material is obtained by reacting 7-hydroxyindazole with an excess of ethylenediamine sulphite in water for 3 hours at 110° C. The compound is obtained in a yield of 67% of theory in the form of colorless crystals which, after recrystallization from ethyl acetate-isopropyl alcohol, melt at 166°–168° C.

EXAMPLE 48

1-Phenoxy-3-[2-(5-methylindazol-4-ylamino)-ethylamino]-propan-2-ol benzoate 3.0 g. Phenyl glycidyl ether and 6.0 g. 5-methyl-4-(2-aminoethylamino)-indazole are dissolved in 12 ml. dimethylformamide and left to stand for 2 days at ambient temperature. The reaction mixture is taken up in a little methylene chloride, shaken out three times with a 10-fold amount of water and the methylene chloride solution is dried and separated column chromatographically on silica gel using, as elution agent, methylene chloride-methanoltriethylamine (100:10:1 v/v/v). By evaporation of the pure fractions, there are obtained 5.2 g. of a dark oil, which is dissolved in a little ethyl acetate, mixed with 2.5 g. benzoic acid, filtered off with suction and recrystallized from ethyl acetate, with the use of active charcoal and fullers' earth. There are obtained 3.3 g. (36% of theory) of the desired product in the form of colorless crystals; m.p. 97°–103° C.

The indazole starting compound used can be obtained by the following steps:
 1. 4-amino-5-methylindazole; m.p. 197°–200° C. (yield 93% of theory) by hydrogenating 4-nitro-5-methylindazole in methanol in the presence of palladium-charcoal;
 2. 5-methyl-4-(2-aminoethylamino)-indazole; m.p. 153°–155° C., recrystallized from water (yield 31% of theory) by reacting 4-amino-5-methylindazole with an excess of ethylenediamine sulphite in ethylene glycol-water (1:1 v/v) for 24 hours at 110° C.

EXAMPLE 49

1-Phenoxy-3-[2-(purin-6-ylamino)-ethylamino]-propan-2-ol 4.5 g. Phenyl glycidyl ether and 14.2 g. 6-(2-aminoethylamino)-purine are stirred in 100 ml. dimethylformamide for 10 hours at 50° C. The reaction mixture is taken up in methylene chloride, shaken out with water, dried and purified chromatographically on a silica gel column in the manner described in Example 25. The product obtained by evaporation of the pure fractions is recrystallized from ethanol. There are obtained 2.3 g. (23% of theory) of the desired product in the form of colorless crystals; m.p. 169°–170° C., with bubble formation.

The 6-(2-aminoethylamino)-purine used as starting material is obtained in good yield by reacting 6-chloropurine with an excess of ethylenediamine.

EXAMPLE 50

1-Phenoxy-3-[2-(2-aminopurin-6-ylamino)-ethylamino]-propan-2-ol 3.5 g. Phenyl glycidyl ether and 8.7 g. 2-amino-6-(2-aminoethylamino)-purine are dissolved in 50 ml. methanol and left to stand for 24 hours at ambient temperature. The methanol is then removed in a vacuum and the residue is dissolved in methylene chloride and purified on a silica gel column using, as elution agent, methylene chloride-methanol (7:3 v/v). The residue obtained by evaporation of the pure fractions is triturated with ethanol and then recrystallized from this solvent. There are obtained 2.0 g. (25% of theory) of the desired product in the form of colorless crystals; m.p. 169°–171° C.

The 2-amino-6-(2-aminoethylamino)-purine used as starting material is obtained by reacting 2-amino-6-chloropurine with an excess of ethylenediamine for 5 hours under reflux. The crude hydrochloride is obtained in a yield of 91% of theory; m.p. >300° C. The crude base is obtained in a yield of 90% of theory in the form of yellowish crystals; m.p. 212°–214° C. with bubble formation.

EXAMPLE 51

1-Phenoxy-3-[2-(pyrazolo[3,4-d]pyrimidin-4-ylamino)-ethylamino]-propan-2-ol 3.2 g. Phenyl glycidyl ether and 5.9 g. 4-(2-aminoethylamino)-pyrazolo[3,4-d]pyrimidine are stirred in 100 ml. methanol for 24 hours at ambient temperature and then for 5 hours at 80° C. Solid material (0.8 g.) is then filtered off with suction, the filtrate is evaporated and the yellowish oil obtained is dissolved in methylene chloride-methanol (9:1 v/v) and purified chromatographically in the manner described in Example 50. There is obtained 1.8 g. (26% of theory) of the desired product in the form of colorless crystals; m.p. 142°–144° C., after recrystallization from ethanol.

The 4-(2-aminoethylamino)-pyrazolo[3,4-d]pyrimidine used as starting material is obtained in a yield of 55% of theory (crude product) (m.p. 170°–172° C. with bubble formation) by reacting 4-chloropyrazolo[3,4-d]-pyrimidine with an excess of ethylenediamine at ambient temperature.

EXAMPLE 52

1-Phenoxy-3-[2-(5-methyl-s-triazolo[1,5-a]pyrimidin-7-ylamino)-ethylamino]-propan-2-ol 3.6 g. Phenyl glycidyl ether and 9.0 g. 5-methyl-7-(2-aminoethylamino)-s-triazolo[1,5-a]pyrimidine are dissolved in dimethyl sulphoxide and left to stand for 48 hours at 45° C. The reaction mixture is then poured into water, extracted with methylene chloride, dried and purified chromatographically in the manner described in Example 28. There are obtained 2.0 g. (24% of theory) of the desired product in the form of colorless crystals; m.p. 126°–127° C., after recrystallization from isopropyl alcohol.

EXAMPLE 53

1-Phenoxy-3-[1,2,3,4-tetrahydroacridin-9-ylamino)-ethylamino]-propan-2-ol 1.6 g. Phenyl glycidyl ether and 5.0 g. 9-(2-aminoethylamino)-1,2,3,4-tetrahydroacridine are dissolved in methanol and boiled under reflux for 1 hour. The reaction mixture is then evaporated and purified chromatographically in the manner described in Example 17. There are obtained 1.0 g. (26% of theory) of the desired product in the form of colorless crystals; m.p. 99°–100° C., recrystallized from isopropyl alcohol.

The 9-(2-aminoethylamino)-1,2,3,4-tetrahydroacridine used as starting material is obtained in the form of a colorless oil by reacting 9-chloro-1,2,3,4-tetrahydroacridine with an excess of ethylenediamine for 12 hours under reflux.

EXAMPLE 54

1-Phenoxy-3-[2-(4-chloro-1,5-dimethylpyrimidin-2(1H)-on-6-ylamino)-ethylamino]-propan-2-ol Solutions of 0.54 g. 1-phenoxy-3-(2-aminoethylamino)-propan-2-ol and of 0.50 g. 4,6-dichloro-1,5-dimethylpyrimidin-2(1H)-one in diethyl ether are combined and left to stand for 24 hours at ambient temperature. The reaction mixture is then filtered with suction to give 0.3 g. of material, a further 0.3 g. of colorless crystals being obtained from the filtrate. These two batches of material are combined and the free base is liberated therefrom with a 2 N aqueous solution of sodium hydroxide. Extraction of the free base with methylene chloride gives 0.5 g. (52% of theory) of a colorless viscous oil.

By adding fumaric acid to an ethanolic solution of the free base, there is obtained the corresponding hydrogen fumarate hemihydrate in the form of colorless crystals: m.p. 179°–180° C.

The 4,6-dichloro-1,5-dimethylpyrimidin-2(1H)-one (colorless crystals; m.p. 106°–108° C.) used as starting material can be obtained by reacting 1,5-dimethylbarbituric acid with an excess of phosphorus oxychloride for 2.5 hours under reflux, followed by the usual working up and purification on silica gel using, as elution agent, methylene chloride-methanol (97:3 v/v).

EXAMPLE 55

1-Phenoxy-3-[2-(4-amino-3,5-dimethylpyrimidin-2(3H)-on-6-ylamino)-ethylamino]-propan-2-ol neutral fumarate A solution of 3.0 g. phenyl glycidyl ether and 8.0 g. 2-(4-amino-3,5-dimethylpyrimidin-2(3H)-on-6-ylamino)-ethylamine in ethanol is left to stand for 48 hours at ambient temperature. The reaction mixture is then evaporated and the residue is purified chromatographically on silica gel using, as elution agent, methylene chloride-methanol-triethylamine (10:3:0.3 v/v/v). The residue of the pure fractions is dissolved in ethanol and mixed with fumaric acid to give a neutral fumarate which is recrystallized from ethanol. There are obtained 3.5 g. (43% of theory) of colorless crystals; m.p. 202°–203° C.

The ethylamine derivative used as starting material can be prepared in the following manner:

1. 6-Amino-4-chloro-1,5-dimethylpyrimidin-2(1H)-one

A solution of 17 g. 4,6-dichloro-1,5-dimethylpyrimidin-2(1H)-one in 500 ml. diethyl ether is stirred at ambient temperature for 96 hours in an atmosphere of dry, gaseous ammonia. The reaction mixture is then filtered with suction and the residue obtained repeatedly stirred up with water. There are obtained 11.1 g. (73% of theory) of colorless crystals; m.p. 254°–256° C.

2. 2-(4-Amino-3,5-dimethylpyrimidin-2(3H)-on-6-ylamino)-ethylamine 11.0 g. of the abovementioned amino compound are heated under reflux for 4 hours with 58 g. ethylenediamine. Excess ethylene diamine is then removed in a vacuum, whereafter the remaining material is dissolved in water and desalted with the ion exchanger "Amberlite" IRA 400 (OH form). The residue obtained by evaporation of the electrolyte-free solution is triturated with a little isopropyl alcohol to give 8.0 g. (64% of theory) of colorless crystals: m.p. 186°–188° C.

EXAMPLE 56

1-Phenoxy-3-[2-(3,5-dimethyl-1-phenylpyrazol-4-ylamino)-ethylamino]-propan-2-ol neutral fumarate A mixture of 3.3 g. phenyl glycidyl ether and 10 g. 4-(2-aminoethylamino)-3,5-dimethyl-1-phenylpyrazole is left to stand for 24 hours at ambient temperature, followed by separation on a silica gel column using, as elution agent, methylene chloride-methanol-triethylamine (10:0.5:0.1 v/v/v). The yellowish oil (6.2 g.) obtained by evaporating the pure fractions is dissolved in ethyl acetate and mixed with a solution of 1.9 g. fumaric acid in ethyl acetate-ethanol. After suction filtration, there are obtained 3.4 g. of product which is recrystallized from ethanol. There are thus obtained 2.5 g. (26% of theory) of colorless crystals: m.p. 124°–125° C.

The pyrazole starting material can be obtained by the following steps:

1. 3,5-Dimethyl-1-phenyl-4-(2-phthalimidoethylamino)-pyrazole

A mixture of 38.1 g. 4-amino-3,5-dimethyl-1-phenylpyrazole, 77.5 g. N-(2-bromoethyl)-phthalimide and 42 g. potassium carbonate in 600 ml. acetonitrile is boiled for 15 hours, with stirring. After cooling, insoluble material is filtered off with suction and the filtrate is evaporated. The residue is stirred with methylene chloride and suction filtered and the filtrate is purified on a silica gel column using, as elution agents, first methylene chloride and then methylene chloride-ethyl acetate (6:4 v/v). There are obtained 41 g. (56% of theory) of a brownish oil.

2. 4-(2-Aminoethylamino)-3,5-dimethyl-1-phenyl pyrazole

This is obtained from the above phthalimide compound by hydrazinolysis. The yield is 82% of theory of a brownish oil.

The corresponding benzoate is, after recrystallization from ethyl acetate, obtained as colorless cyrstals: m.p. 136°–138° C.

EXAMPLE 57

1-Phenoxy-3-[2-benztriazol-4-ylamino)-ethylamino]-propane-2-ol benzoate 0.7 g. phenyl glycidyl ether and 1.5 g. 4-(2-aminoethylamino)-benztriazole in 10 ml. dimethylformamide are heated for 3 hours at 80° C., with stirring. The solvent is removed in a vacuum, the residue is digested with methylene chloride-methanol (10:1 v/v), the solution obtained is shaken with water, dried and purified over a silica gel column using, as elution agent, methylene chloride-methanol saturated with ammonia (10:1 v/v). By evaporation of the pure fractions, there is obtained 0.3 g. of a light-colored, viscous mass. This is dissolved in ethyl acetate, mixed with 0.2 g. benzoic acid, filtered with suction and recrystallized from ethyl acetate. The benzoate is obtained in the form of colorless crystals: m.p. 131°–133° C.

The 4-(2-aminoethylamino)-benztriazole used as starting material can be obtained as follows:

13.3 g. 4-Hydroxybenztriazole (very impure) are stirred with 146 g. ethylenediamine sulphite in 146 ml. water for 2 hours at 100°–110° C. After cooling, the reaction mixture is mixed with 500 ml. methanol, the salts formed are filtered off with suction and the filtrate is desalted with the ion exchanger "Amberlite" IRA 400 (OH form, pretreated with ammonium carbonate). The eluate is evaporated and the solidified mass obtained is triturated wih a little concentrated aqueous ammonia solution. The product is filtered off with suction and then washed with a little water. There is obtained 1.3 g. (10% theory) of beige crystals: m.p. 181°–183° C.

By adding oxalic acid to an ethanolic solution of the product, there can be obtained a sesquioxalate in the form of beige crystals: m.p. 169°–171° C. (decomp.).

EXAMPLE 58

1-Phenoxy-3-[2-(pyrimido[4,5,6]indol-4-ylamino)-ethylamino]-propan-2-ol neutral fumarate hydrate 1.22 g. phenyl glycidyl ether and 3.7 g. 1-(2-aminoethylamino)-pyrimido[4,5-d]indole (prepared by reacting 1-chloropyrimido[4,5-b]indole with an excess of ethylenediamine) are stirred for 7 hours at 50° C., in 20 ml. dimethylformamide. The reaction mixture is then evaporated and the residue is purified chromatographically over a silica gel column using, as elution agent, methylene chloride-methanol-triethylamine (10:2:0.3 v/v/v). The residue obtained by evaporation of the pure fractions is mixed in ethyl acetate-ethanol with fumaric acid and the product obtained is recrystallized from ethanol. There is obtained 0.3 g. (15% of theory) of colorless crystals: m.p. 187°–188° C.

EXAMPLE 59

Tablets are prepared, each of which contains 10 mg. 1-(4-fluorophenoxy)-3-[2-(2,6-dimethylphenylamino)-ethylamino]-propan-2-ol. The tablets are produced according to the following formulation:

1-(4-fluorophenoxy)-3-[2-(2,6-dimethyl-phenylamino)-ethylamino]-propan-2ol: 10 g.
lactose: 80 g.
starch: 29 g.
magnesium stearate: 1 g.

The active compound is finely powdered and mixed with the lactose and starch and the mixture is granulated in conventional manner. The magnesium stearate is added to the granulate and the mixture used for pressing 1000 tablets, each of which has a weight of 0.12 g.

Test Report

For the tests, mongrel dogs of both sexes were available. In a preparatory operation, catheters had been inserted under aseptic conditions into the Arteria and *Vena femoralis* and, through the myocardium, into the left ventricle. The tests were begun not less than ten days after this operation, when the animals were again in a clinically healthy state.

Throughout the test, during which the animals were awake, the arterial blood pressure was determined by means of a catheter and an elecromechanical transducer. In addition, the pressure in the left ventricle was continuously measured by means of a tip manometer which had been introduced into the verticle catheter and advanced as far as the heart, and from that pressure the differentiation based on the time dp/dt max was determined. The heart rate (f cor) was computed by counting the heart beats at a fast chart speed at given times of measurement.

The substances were infused at a dose rate of 0.25 $\mu$g/kg/min over a period of 60 minutes, and this was followed by 30 minutes of observation. In the case of some of the substances, the doses were increased by a factor of 10, or the doses were injected in a protracted manner in logarithmic progression, in order to cover as wide a range of dosage variation as possible.

From the logarithm of the dose administered at a given time and the effect on dp/dt max and the heart rate (f cor), respectively, a linear regression was computed. From this it was possible to calculate the doses $DE_{+30\%}$ and $DE_{+50\%}$ ($\mu$g/kg) which produced an increase in the initial values of dp/dt max and of f cor by 30% and 50%, respectively. (Example, see Table 1.)

The results of the comparison compounds and of the novel s substances are presented in Table 2. From that table it is apparent that while the comparison compound A, 1-phenoxy-3-[2-(2,6-dimethyl-phenylamino)-ethylamino]-propan-2-ol (Example 7 in German application DOS 28 44 497, VEB Dresden) has a good cardiotonic effect (an increase in dp/dt max), at the same dose rate it also increases the heart rate, which is undesirable as a matter of principle since it taxes the heart too much.

As a measure of the quality of the substances, it was first sought to determine the doses which increase cardiac activity (dp/dt max) and the heart rate (f cor) by 30% and 50%, respectively. When a quotient is derived by dividing $DE_{+30\%\ f\ cor}$ by $DE_{+30\%\ dp/dt}$, the substances having a high quotient are particularly useful since based on the dose the increase in cardiac activity with these substances is greater than the increase in the heart rate. Thus, the higher the quotient, the better the substance. However, consistently low doses cannot be regarded as a criterion for a particularly favorable effect. What matters is the ratio between effect on heart rate and effect on contractility.

The comparison substance B, 1-phenoxy-3-[2-(1,3-dimethyl-pyrimidine-2,4-dione-6-yl-amino)-ethylamino]-propan-2-ol (Example 1 German application DOS 28 19 629, Cassella), has no cardiotonic effect.

TABLE 1
TEST OF SELECTED SUBSTANCES FOR CARDIOTONIC EFFECT ON WAKE DOGS $\bar{p}a$ = Mean arterial blood pressure (mm Hg)
$f_{cor}$ = Heart rate (beats/min)
dp/dt = Rate of increase in pressure in left ventricle (mm Hg/sec)
$DE_{+30\%}$ and $DE_{+50\%}$ = Dose producing an increase in the initial values of 30% and 50%, respectively (μg/kg)

| Substance | Measured value | Initial value | 5<br>1,25 | 10<br>2,5 | 15<br>3,75 | 30<br>7,5 | 45<br>11,25 | 60<br>15,0 | $DE_{+30\%}$ | $DE_{+50\%}$ | Regressive equation |
|---|---|---|---|---|---|---|---|---|---|---|---|
| A* | $\bar{p}a$ | 96 | 97 | 99 | 98 | 98 | 105 | 105 | | | |
| | $f_{cor}$ | 92 | 93 | 115 | 108 | 123 | 141 | 149 | 4,5 | 10,9 | y = 53log X +95,5 |
| | dp/dt | 2,15 | 2,05 | 2,48 | 2,60 | 2,90 | 3,68 | 3,48 | 4,4 | 8,8 | y = 67log X +86,5 |
| Substance | $\bar{p}a$ | 98 | 97 | 106 | 100 | 105 | 106 | 102 | | | |
| from Example 15 | $f_{cor}$ | 55 | 57 | 77 | 63 | 65 | 85 | 103 | 3,81 | 8,55 | y = 57log X +96,9 |
| | dp/dt | 2,30 | 3,20 | 3,30 | 3,40 | 3,80 | 4,40 | 4,80 | 1,55 | 2,74 | y = 81log X +114,4 |

*1-Phenoxy-3-[2-(2,6-dimethylphenylamino)-ethylamino]-propane-2-ole
(Example 7 from German patent application DOS 28 44 497, VEB Dresden)
The examples are cited merely for elucidation of the method of evaluation

TABLE 2
DATA ON FURTHER COMPOUNDS DETERMINED ANALOGOUSLY TO TABLE 1

| Example No. | $DE_{+30\%}$ (μg/kg) $f_{cor}$ | | | $DE_{+50\%}$ (μg/kg) $f_{cor}$ | | |
|---|---|---|---|---|---|---|
| | dp/dt | $f_{cor}$ | dp/dt | dp/dt | $f_{cor}$ | dp/dt |
| A* | 4,4 | 4,5 | 1,0 | 8,8 | 10,9 | 1,2 |
| B** | >150 | >150 | — | >150 | >150 | — |
| 15 | 1,55 | 3,81 | 2,46 | 2,74 | 8,55 | 3,15 |
| 11 | 22,6 | >150 | >6,6 | 47,1 | >150 | >3,2 |
| 21 | 45,4 | 311 | 6,9 | 155 | 669 | 4,3 |
| 48 | 21,2 | 70,8 | 3,3 | 85,1 | 742 | 8,7 |
| 1 | 9,7 | 18,7 | 1,9 | 36,8 | 75,5 | 2,1 |
| 42 | 236 | 2734 | 11,6 | 589 | 8979 | 15,2 |
| 29 | 72,7 | 160 | 2,20 | 110 | 348 | 3,16 |
| 19 | 27,7 | 82,8 | 2,99 | 39,0 | 135 | 3,46 |

*1-Phenoxy-3-[2-(2,6-dimethylphenylamino)-ethylamino]-propane-2-ole
(Example 7 from German patent application DOS 28 44 497, VEB Dresden)
**1-Phenoxy-3-[2-(1,3-dimethyl-pyrimidine-2,4-dione-6-yl-amino)-ethylamino]-propane-2-ole
(Example 1 from German pat. appl. DOS 28 19 629, Cassella)

The dosage administered depends upon the age, the state of health and the weight of the recipient, the extent of the disease, the nature of other treatments possibly carried out simultaneously, the frequency of the treatment and the nature of the desired action. Usually, the oral daily dosage of the active compound is 0.1 to 200 mg./kg. of body weight. Normally, 0.5 to 150 and preferably 1.0 to 100 mg./kg./day in one or more administrations per day are effective for the achievement of the desired results.

It will be appreciated that the instant specification and examples are set forth by way of illustration and not limitation, and that various modifications and changes may be made without departing from the spirit and scope of the present invention.

We claim:

1. An aryloxypropanolamine of the formula

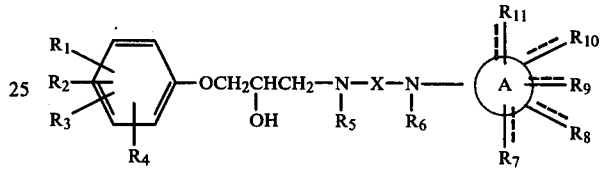

wherein
$R_1$, $R_2$, $R_3$ and $R_4$ each independently is hydrogen, chlorine, bromine, fluorine, $C_{1-4}$-alkyl, cyano, carboxamido, hydroxyl, $C_{2-5}$-alkenyloxy or phenyl-$C_{1-4}$-alkoxy,
$R_5$ and $R_6$ each independently is hydrogen or $C_{1-4}$-alkyl,
X is an ethylene or propylene radical,
A is an indazole connected to the —X—N($R_6$)— chain through a carbon atom,
$R_7$, $R_8$, $R_9$, $R_{10}$ and $R_{11}$ each independently is, or two of them together are, hydrogen, amino, $C_{1-4}$-alkyl or $C_{2-5}$-alkenyl;
or a pharmacologically compatible salt thereof.

2. A compound according to claim 1, wherein such compound is 1-phenoxy-3-[2-(4-indazolylamino)-ethylamino]-propan-2-ol or a pharmacologically acceptable salt thereof.

3. A composition for combating cardiac and circulatory diseases comprising an amount effective therefor of a compound or salt according to claim 1 in admixture with a pharmacologically acceptable diluent.

4. A method of combating cardiac and circulatory diseases comprising administering to a patient suffering therefrom an amount effective therefor of a compound or salt according to claim 1.

5. A method according to claim 4, wherein the material administered is 1-phenoxy-3-[2-(4-indazolylamino)-ethylamino]-propan-2-ol or a pharmacologically compatible salt thereof.

* * * * *